US012751768B2

(12) United States Patent
Pollock et al.

(10) Patent No.: US 12,751,768 B2
(45) Date of Patent: Oct. 6, 2026

(54) CUSTOMIZED PATIENT-SPECIFIC ORTHOPAEDIC SURGICAL INSTRUMENT USING PATIENT-SPECIFIC CONTACTING BODIES AND PARAMETRIC FIXED GEOMETRY

(71) Applicant: DePuy Synthes Products, Inc., Raynham, MA (US)

(72) Inventors: Shawnoah S. Pollock, South Bend, IN (US); Anwar Mohammed, Warsaw, IN (US); Randy P. Mangen, Yorkshire, OH (US); Francis G. Metelues, Fort Wayne, IN (US); R. Patrick Courtis, Boston, MA (US); Luke J. Aram, Winona Lake, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 487 days.

(21) Appl. No.: 18/512,285

(22) Filed: Nov. 17, 2023

(65) Prior Publication Data

US 2024/0081912 A1 Mar. 14, 2024

Related U.S. Application Data

(62) Division of application No. 17/039,373, filed on Sep. 30, 2020, now Pat. No. 11,819,280.

(51) Int. Cl.
*A61B 34/10* (2016.01)
*A61B 17/15* (2006.01)
(Continued)

(52) U.S. Cl.
CPC ............ *A61B 34/10* (2016.02); *A61B 17/155* (2013.01); *B33Y 50/00* (2014.12); *B33Y 80/00* (2014.12);
(Continued)

(58) Field of Classification Search
CPC ........ B33Y 50/00; B33Y 80/00; G61H 20/40; A61B 17/155; A61B 2034/102;
(Continued)

(56) References Cited

U.S. PATENT DOCUMENTS

| | | | |
|---|---|---|---|
| 8,265,949 B2 | 9/2012 | Haddad | |
| 8,361,076 B2 | 1/2013 | Roose et al. | |

(Continued)

FOREIGN PATENT DOCUMENTS

| | | | |
|---|---|---|---|
| WO | 9325157 | A1 | 12/1993 |
| WO | 2017204832 | A1 | 11/2017 |

*Primary Examiner* — Sameh R Boles

(74) *Attorney, Agent, or Firm* — Barnes & Thornburg LLP

(57) ABSTRACT

A model production device generates one or more contact bodies of a patient-specific surgical instrument model based on a parameterized model of a patient's bone. The parameterized model includes a predetermined number of polygons each having a predetermined position relative to the patient's anatomy. The parameterized model may be generated based on a three-dimensional model that was generated based on multiple images of the patient's bone. The model production device adds parametric fixed geometry to the patient-specific surgical instrument model based on the parameterized model and subtracts the three-dimensional model of the patient's bone from the patient-specific surgical instrument model. Each contacting body may be positioned at a high-confidence part of the parametric model, and the parametric fixed geometry may be positioned at a low-confidence part. A patient-specific surgical instrument may be manufactured based on the patient-specific surgical instrument model.

14 Claims, 13 Drawing Sheets

(51) Int. Cl.

| | |
|---|---|
| ***B33Y 50/00*** | (2015.01) |
| ***B33Y 80/00*** | (2015.01) |
| ***G16H 20/40*** | (2018.01) |
| ***G16H 50/50*** | (2018.01) |
| *A61B 17/00* | (2006.01) |

(52) U.S. Cl.
CPC ............. *G16H 20/40* (2018.01); *G16H 50/50* (2018.01); *A61B 2017/00526* (2013.01); *A61B 2034/102* (2016.02); *A61B 2034/105* (2016.02); *A61B 2034/108* (2016.02)

(58) Field of Classification Search
CPC ........ A61B 2034/105; A61B 2034/108; A61B 2017/00526; A61B 34/10
See application file for complete search history.

(56) References Cited

U.S. PATENT DOCUMENTS

| | | | |
|---|---|---|---|
| 8,425,524 B2 | 4/2013 | Aker et al. | |
| 8,594,395 B2 | 11/2013 | Roose et al. | |
| 8,617,170 B2 | 12/2013 | Ashby et al. | |
| 8,641,721 B2 | 2/2014 | Aram et al. | |
| 8,808,302 B2 | 8/2014 | Roose et al. | |
| 8,979,855 B2 | 3/2015 | Aram et al. | |
| 8,992,538 B2 | 3/2015 | Keefer | |
| 9,131,945 B2 | 9/2015 | Aram et al. | |
| 9,138,247 B2 | 9/2015 | Aram et al. | |
| 9,299,138 B2 | 3/2016 | Zellner et al. | |
| 10,098,761 B2 | 10/2018 | Sherman et al. | |
| 10,149,722 B2 | 12/2018 | Aram et al. | |
| 10,251,654 B2 | 4/2019 | Fritzinger | |
| 10,537,343 B2 | 1/2020 | Fritzinger | |
| 10,631,878 B2 | 4/2020 | Fritzinger | |
| 10,856,891 B2 | 12/2020 | Rhodes et al. | |
| 10,874,404 B2 | 12/2020 | Langhorn et al. | |
| 11,051,829 B2 | 7/2021 | Courtis et al. | |
| 11,090,085 B2 | 8/2021 | Rhodes et al. | |
| 11,134,908 B2 | 10/2021 | Pollock et al. | |
| 11,229,519 B2 | 1/2022 | Radermacher et al. | |
| 11,304,710 B2 | 4/2022 | Rhodes et al. | |
| 11,348,216 B2 | 5/2022 | Pollock et al. | |
| 2010/0185202 A1 | 7/2010 | Lester et al. | |
| 2012/0209394 A1 * | 8/2012 | Bojarski | A61F 2/4202 623/18.11 |
| 2013/0150862 A1 | 6/2013 | Aram et al. | |
| 2016/0287337 A1 | 10/2016 | Aram et al. | |
| 2016/0317312 A1 | 11/2016 | Bojarski et al. | |
| 2022/0096157 A1 | 3/2022 | Pollock et al. | |

* cited by examiner

CUSTOMIZED PATIENT-SPECIFIC ORTHOPAEDIC SURGICAL INSTRUMENT USING PATIENT-SPECIFIC CONTACTING BODIES AND PARAMETRIC FIXED GEOMETRY

The present application is a divisional of, and claims priority to, U.S. patent application Ser. No. 17/039,373, now U.S. Pat. No. 11,819,280, entitled "CUSTOMIZED PATIENT-SPECIFIC ORTHOPAEDIC SURGICAL INSTRUMENT USING PATIENT-SPECIFIC CONTACTING BODIES AND PARAMETRIC FIXED GEOMETRY," which was filed on Sep. 30, 2020, the entirety of which is hereby incorporated by reference.

TECHNICAL FIELD

The present disclosure relates generally to orthopaedic surgical instruments and, more particularly, to customized patient-specific orthopaedic surgical instruments.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. In a hip replacement surgical procedure, a patient's natural acetabulum is replaced by a prosthetic cup and a patient's natural femoral head is partially or totally replaced by a prosthetic stem and femoral ball.

To facilitate the replacement of the natural joint with a prosthesis, orthopaedic surgeons use a variety of orthopaedic surgical instruments such as, for example, cutting blocks, drill guides, milling guides, and other surgical instruments. Typically, the orthopaedic surgical instruments are reusable and generic with respect to the patient such that the same orthopaedic surgical instrument may be used on a number of different patients during similar orthopaedic surgical procedures.

The orthopaedic surgical instruments may also be customized to a specific patient. Such "customized patient-specific orthopaedic surgical instruments" are single-use surgical tools for use by a surgeon in performing an orthopaedic surgical procedure that is intended, and configured, for use on a particular patient. It should be appreciated that these instruments are distinct from standard, non-patient-specific orthopaedic surgical instruments that are intended for use on a variety of different patients. These customized patient-specific orthopaedic surgical instruments are distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

SUMMARY

According to one aspect, a method includes generating a contacting body of a patient-specific surgical instrument model based on a parameterized model of a patient's bone, wherein the parameterized model comprises a predetermined number of polygons, and wherein each polygon has a predetermined position relative to the patient's anatomy. Generating the contacting body includes determining a bounding spline based on a predetermined set of polygons of the parametrized model; generating a bounded surface surrounded by the bounding spline; and extending the bounded surface away from the parametrized model of the patient's bone and toward the parameterized model of the patient's bone to generate the contacting body, wherein the contacting body intersects a surface of the parameterized model. The method further includes subtracting a three-dimensional model of the patient's bone from the patient-specific surgical instrument model to create a contacting surface, wherein the contacting surface is positioned on the contacting body; and manufacturing a patient-specific surgical instrument based on the patient-specific surgical instrument model in response to subtracting the three-dimensional model. In an embodiment, the patient-specific surgical instrument comprises a femoral cutting guide.

In an embodiment, each polygon of the predetermined set of polygons has a predetermined index in the parameterized model. In an embodiment, determining the bounding spline includes identifying the predetermined set of polygons; setting a control point at a center of each polygon of the predetermined set of polygons; and generating the bounding spline based on the control points.

In an embodiment, the method further includes adding a bridging body connected to the contacting body of the patient-specific surgical instrument model based on the parameterized model, wherein the bridging body intersects the surface of the parametrized model and wherein the bridging body has a parametric fixed geometry. Adding the bridging body includes determining a parameter of the parametric fixed geometry of the bridging body based on the parameterized model. Subtracting the three-dimensional model includes subtracting the three-dimensional model in response to adding the bridging body. The contacting surface is further positioned on the bridging body. In an embodiment, determining the parameter of the parametric fixed geometry comprises determining a length, a width, or a thickness based on a position of a polygon of the parametrized model. In an embodiment, determining the parameter of the parametric fixed geometry includes determining a location of the bridging body relative to the parameterized model. In an embodiment, determining the location of the bridging body relative to the parameterized model includes determining the location of the bridging body relative to the bounding spline. In an embodiment, the method further includes adding a second fixed geometry to the patient-specific surgical instrument model, wherein the second fixed geometry comprises a non-contacting surface.

In an embodiment, generating the contacting body includes generating the contacting body at a high-confidence part of the parameterized model; and adding the parametric fixed geometry includes adding the parametric fixed geometry at a low-confidence part of the parameterized model. In an embodiment, the low-confidence part includes a part of the parameterized model associated with a location of an osteophyte of the patient's bone, and the high-confidence part includes a part of the parameterized model associated with a location of a condylar surface or a femoral cortex of the patient's bone. In an embodiment, the high-confidence part of the parameterized model includes polygons with an associated accuracy that exceeds a predetermined accuracy threshold.

In an embodiment, the method further includes generating the three-dimensional model of the patient's bone based on a plurality of images of the patient's bone; and parameterizing the three-dimensional model of the patient's bone to generate the parameterized model. In an embodiment, the method further includes generating the parameterized model based on a plurality of images of the patient's bone, wherein the parameterized model comprises the three-dimensional model.

According to another aspect, a patient-specific surgical instrument includes a first contacting body and a bridging body coupled to the first contacting body. The first contacting body has a perimeter based on a bounding spline determined from a parameterized model of a patient's bone. The parameterized model comprises a predetermined number of polygons, and each polygon has a predetermined position relative to the patient's anatomy. The bridging body has a shape determined based on a parametric fixed geometry with a parameter determined from the parameterized model. The first contacting body and the bridging body are configured to contact the patient's bone.

In an embodiment, the patient-specific surgical instrument further includes a second contacting body having a perimeter determined based on a second bounding spline determined from the parameterized model, wherein the second body is configured to contact the patient's bone. The bridging body couples the first contacting body and the second contacting body.

In an embodiment, the patient-specific surgical instrument further includes a fixed geometry component coupled to the bridging body and the contacting body, wherein the fixed geometry component includes a non-contacting surface.

According to another aspect, one or more computer-readable media include a plurality of instructions that, when executed by a computing device, cause the computing device to generate a contacting body of a patient-specific surgical instrument model based on a parameterized model of a patient's bone, wherein the parameterized model comprises a predetermined number of polygons, and wherein each polygon has a predetermined position relative to the patient's anatomy, wherein to generate the contacting body comprises to: (i) determine a bounding spline based on a predetermined set of polygons of the parametrized model, (ii) generate a bounded surface surrounded by the bounding spline, and (iii) extend the bounded surface away from the parametrized model of the patient's bone and toward the parameterized model of the patient's bone to generate the contacting body, wherein the contacting body intersects a surface of the parameterized model; add a bridging body connected to the contacting body of the patient-specific surgical instrument model based on the parameterized model, wherein the bridging body intersects the surface of the parametrized model and wherein the bridging body has a parametric fixed geometry, wherein to add the bridging body comprises to determine a parameter of the parametric fixed geometry of the bridging body based on the parameterized model; and subtract a three-dimensional model of the patient's bone from the patient-specific surgical instrument model to create a contacting surface, wherein the contacting surface is positioned on the contacting body and the bridging body.

In an embodiment, the one or more computer-readable media further include a plurality of instructions that, when executed by the computing device, cause the computing device to manufacture a patient-specific surgical instrument based on the patient-specific surgical instrument model in response to subtraction of the three-dimensional model.

In an embodiment, to generate the contacting body includes to generate the contacting body at a high-confidence part of the parameterized model; and to add the parametric fixed geometry includes to add the parametric fixed geometry at a low-confidence part of the parameterized model.

BRIEF DESCRIPTION OF THE DRAWINGS

The detailed description particularly refers to the following figures, in which.

DETAILED DESCRIPTION OF THE DRAWINGS

Figure 1:
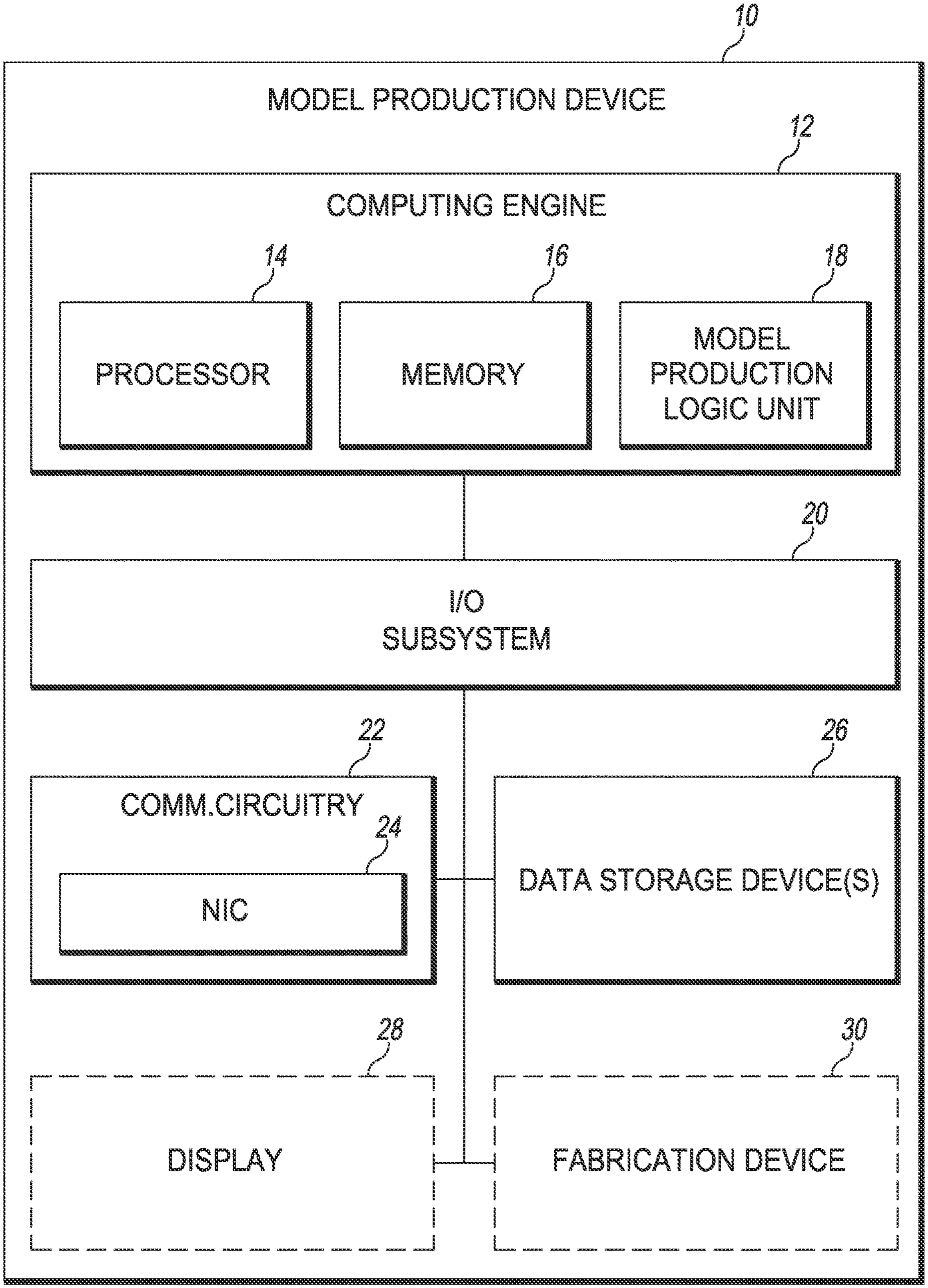
FIG. 1 is a simplified block diagram of one embodiment of a model production system for producing a patient-specific surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

Referring now to FIG. 1, a model production device 10 for producing a patient-specific surgical instrument processes a parametric model of a patient's bone, which may be generated from a set of two-dimensional images or otherwise generated. The model production device 10 generates a model of the patient-specific surgical instrument by determining one or more bounding splines or other interpolating curves based on the parametric model and generating contacting bodies based on the bounding splines. Each contacting body is an island, pad, separate body, or other portion of the patient-specific surgical instrument with geometry that is automatically generated from the parametric model and that is configured to contact a portion of the patient's bone. The contacting bodies are connected together with one or more bridging bodies. Unlike the contacting bodies, the bridging bodies have parametric, fixed geometry that is based on a predetermined shape that may be modified by one or more parameters. For example, each bridging body may be based on a rectangular shape with parameters such as width, length, and thickness as described further below. After connecting the contacting bodies with bridging bodies, the model is further modified to generate the final model used for producing the surgical instrument.

The model production device 10 may position the contacting bodies in locations where the parametric model is more accurate relative to the patient's bony anatomy, and may position the bridging bodies (with parametric, fixed geometry) in locations where the parametric model is less accurate. Thus, as compared to other systems, the model production device 10 may improve stability of the surgical instrument when positioned on the patient's bone. Additionally, the model production device 10 described herein may generate the surgical instrument model automatically or otherwise generate the surgical instrument model with reduced human interaction as compared to other systems.

What is meant herein by the term "customized patient-specific orthopaedic surgical instrument" or "customized patient-specific instrumentation" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient-specific orthopaedic surgical instruments (i.e., "patient-universal instruments" such as patient-universal cutting blocks) that are intended for use on a variety of different patients and were not fabricated or customized to any particular patient. Additionally, it should be appreciated that, as used herein, the term "customized patient-specific orthopaedic surgical instrument" is distinct from orthopaedic prostheses or implants, whether patient-specific or generic, which are surgically implanted in the body of the patient. Rather, an orthopaedic surgeon uses customized patient-specific orthopaedic surgical instruments to assist in the implantation of orthopaedic prostheses. Examples of "customized patient-specific orthopaedic surgical instruments" include customized patient-specific drill/pin guides, customized patient-specific tibial cutting blocks, customized patient-specific femoral cutting blocks, and customized patient-specific alignment guides.

As shown in FIG. 1, the illustrative model production device 10 may be embodied as a computing device (e.g., a computer) that includes a computing engine (also referred to herein as "computing engine circuitry") 12, an input/output (I/O) subsystem 20, communication circuitry 22, and one or more data storage devices 26. Of course, in other embodiments, the model production device 10 may include other or additional components, such as those commonly found in a computer (e.g., a display, peripheral devices, etc.). Additionally, in some embodiments, one or more of the illustrative components may be incorporated in, or otherwise form a portion of, another component. The model production device 10 may be embodied as a single computing device, a server, a workstation, or a collection of servers and associated devices. For example, in some embodiments, the model production device 10 may be embodied as a "virtual server" formed from multiple computing devices distributed across a network and operating in a public or private cloud. Accordingly, although the model production device 10 is illustrated in FIG. 1 and described below as embodied as a single computing device, it should be appreciated that the model production device 10 may be embodied as multiple devices cooperating together to facilitate the functionality described below.

The computing engine 12 may be embodied as any type of device or collection of devices capable of performing various computing functions described below. In some embodiments, the computing engine 12 may be embodied as a single device such as an integrated circuit, an embedded system, a field-programmable gate array (FPGA), a system-on-a-chip (SOC), or other integrated system or device. In the illustrative embodiment, the computing engine 12 includes or is embodied as a processor 14, a memory 16, and a model production logic unit 18. The processor 14 may be embodied as any type of processor capable of performing the functions described herein. For example, the processor 14 may be embodied as a multi-core processor(s), a microcontroller, or other processor or processing/controlling circuit. In some embodiments, the processor 14 may be embodied as, include, or be coupled to an FPGA, an application specific integrated circuit (ASIC), reconfigurable hardware or hardware circuitry, or other specialized hardware to facilitate performance of the functions described herein.

The main memory 16 may be embodied as any type of volatile (e.g., dynamic random access memory (DRAM), etc.) or non-volatile memory or data storage capable of performing the functions described herein. Volatile memory may be a storage medium that requires power to maintain the state of data stored by the medium. In some embodiments, all or a portion of the main memory 16 may be integrated into the processor 14. In operation, the main memory 16 may store various software and data used during operation such as one or more applications, data operated on by the application(s) (e.g., two-dimensional images, three-dimensional models, parametric models, bounding splines, fixed geometry, etc.), libraries, and drivers.

In the illustrative embodiment, the model production device 10 includes the model production logic unit 18, which may be embodied as software or any device or circuitry (e.g., a co-processor, reconfigurable circuitry, an application specific integrated circuit (ASIC), a field programmable gate array (FPGA), etc.) configured to perform the model production operations described above (e.g., offloading those operations from a general purpose processor of the model production device 10).

The computing engine 12 is communicatively coupled to other components of the model production device 10 via the I/O subsystem 20, which may be embodied as circuitry and/or components to facilitate input/output operations with the computing engine 12 (e.g., with the processor 14 and/or the main memory 16) and other components of the model production device 10. For example, the I/O subsystem 20 may be embodied as, or otherwise include, memory controller hubs, input/output control hubs, integrated sensor hubs, firmware devices, communication links (e.g., point-to-point links, bus links, wires, cables, light guides, printed circuit board traces, etc.), and/or other components and subsystems to facilitate the input/output operations. In some embodiments, the I/O subsystem 20 may form a portion of a system-on-a-chip (SoC) and be incorporated, along with one or more of the processor 14, the main memory 16, and other components of the model production device 10, into the computing engine 12.

The communication circuitry 22 may be embodied as any communication circuit, device, or collection thereof, capable of enabling communications over a network between the model production device 10 and another computing device. The communication circuitry 22 may be configured to use any one or more communication technology (e.g., wired or wireless communications) and associated protocols (e.g., Ethernet, Wi-Fi®, WiMAX, Bluetooth®, cellular, etc.) to effect such communication.

The illustrative communication circuitry 22 includes a network interface controller (NIC) 24. The NIC 24 may be embodied as one or more add-in-boards, daughter cards, network interface cards, controller chips, chipsets, or other devices that may be used by the model production device 10 to connect with another computing device. In some embodiments, the NIC 24 may be embodied as part of a system-on-a-chip (SoC) that includes one or more processors, or included on a multichip package that also contains one or more processors. In some embodiments, the NIC 24 may include a local processor (not shown) and/or a local memory (not shown) that are both local to the NIC 24. In such embodiments, the local processor of the NIC 24 may be capable of performing one or more of the functions of the computing engine 12 described herein. Additionally or alternatively, in such embodiments, the local memory of the NIC 24 may be integrated into one or more components of the model production device 10 at the board level, socket level, chip level, and/or other levels.

The one or more illustrative data storage devices 26 may be embodied as any type of devices configured for short-term or long-term storage of data such as, for example, memory devices and circuits, memory cards, hard disk drives, solid-state drives, or other data storage devices. Each data storage device 26 may include a system partition that stores data and firmware code for the data storage device 26. Each data storage device 26 may also include one or more operating system partitions that store data files and executables for operating systems.

As shown in FIG. 1, in some embodiments the model production device 10 may include a display 28 and/or a fabrication device 30. The display 30 may be embodied as any type of display capable of displaying digital information such as a liquid crystal display (LCD), a light emitting diode (LED), a plasma display, a cathode ray tube (CRT), or other type of display device. The display 28 may be used, for example, to visualize one or more three-dimensional models, including models of the patient's bone and/or a customized patient-specific surgical instrument. The fabrication device 30 may be embodied as a three-dimensional printer or other output device capable of fabricating a patient-specific surgical instrument as described herein. The model production device 10 may also include any number of additional input/output devices, interface devices, sensors, and/or other peripheral devices. For example, in some embodiments, model production device 10 may include a touch screen, graphics circuitry, keyboard, mouse, speaker system, microphone, network interface, and/or other input/output devices, interface devices, and/or peripheral devices.

Figure 2A:
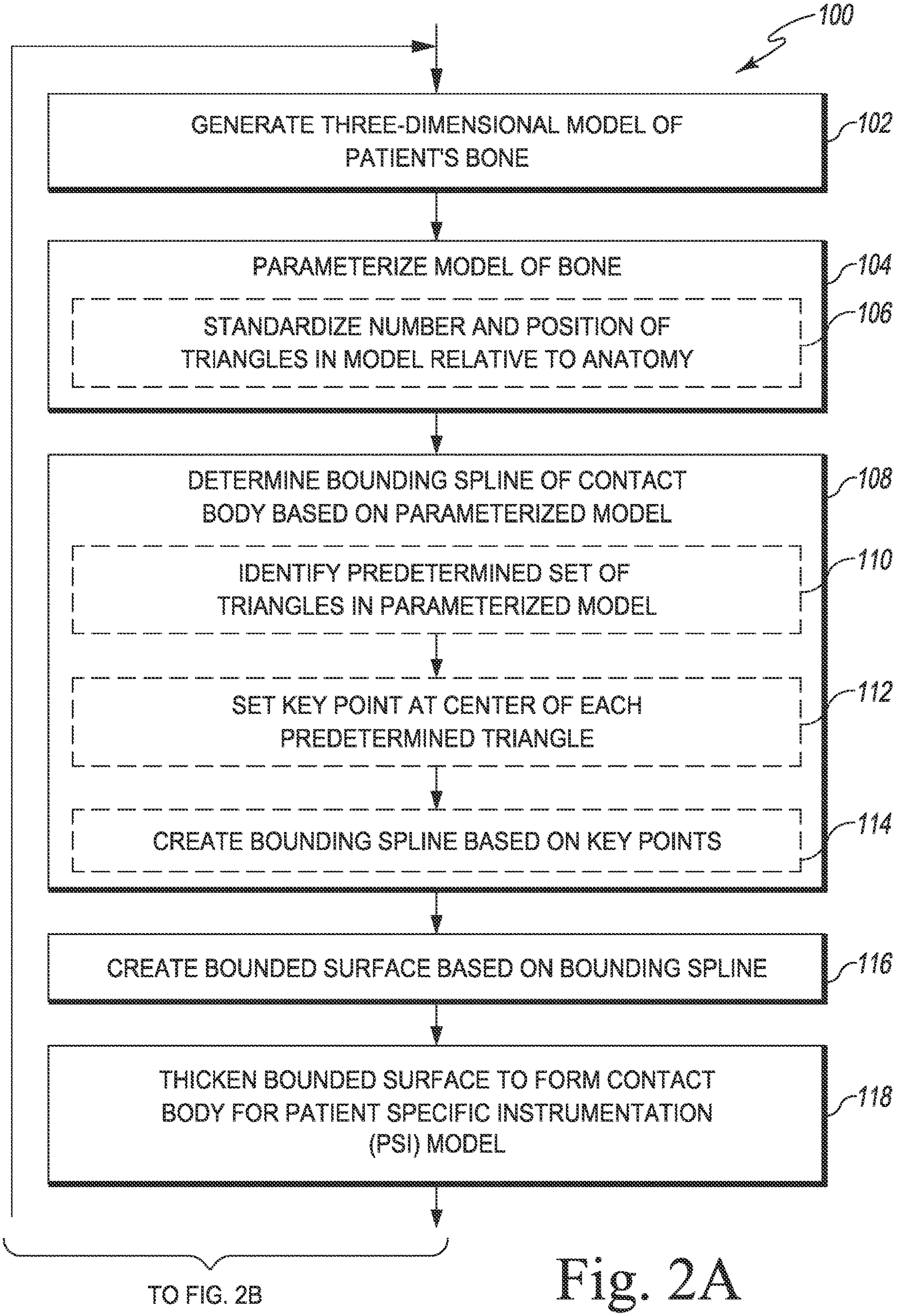
FIGS. 2A and 2B are a simplified flow diagram of a method that may be performed by the model production device of FIG. 1 for producing a customized patient-specific surgical instrument.
Figure 2B:
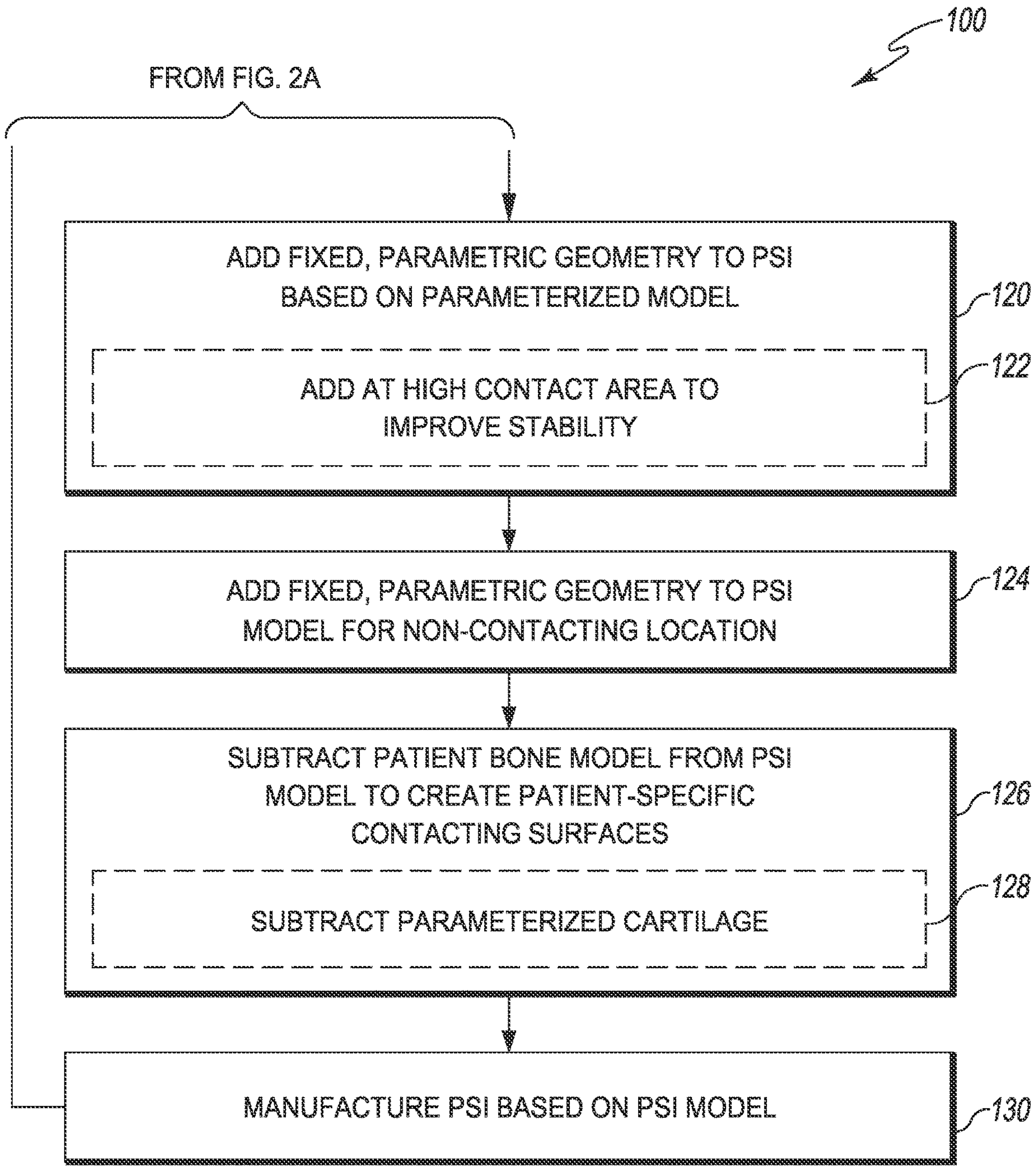

Referring now to FIGS. 2A and 2B, the model production device 10, in operation, may execute a method 100 for producing a patient-specific surgical instrument. The method 100 begins with block 102, in which the model production device 10 generates a three-dimensional model of a patient's bone. For example, a three-dimensional model may be generated for a patient's femur. The three-dimensional model may be developed based on imaging of the patient's bone (e.g., the patient's femur). To generate the three-dimensional model, a number of medical images of the relevant bony anatomy or joint of the patient are generated. To do so, an orthopaedic surgeon or other healthcare provider may operate an imaging system to generate the medical images. The medical images may be embodied as any number and type of medical images capable of being used to generate a three-dimensional rendered model of the patient's bony anatomy or relevant joint. For example, the medical images may be embodied as a number of X-ray images or other two-dimensional images from which a three-dimensional rendered model of the patient's relevant bony anatomy may be generated. Additionally, in some embodiments, the medical image may be enhanced with a contrast agent designed to highlight the cartilage surface of the patient's joint. Additionally or alternatively, the medical images may be embodied as any number of computed tomography (CT) images, magnetic resonance imaging (MRI) images, or other three-dimensional medical images.

After generating or otherwise receiving the medical images, a three-dimensional model of the patient's bone is generated based on the medical images. In one embodiment, a computing device or other modeling system (e.g., the model production device 10 or another device) may perform an x-ray segmentation process to model the patient's bone based on the input x-ray images. In that segmentation process, the computing device receives a set of x-ray images. The computing device accesses a bone library that includes models or other measurements of many sample bones. The computing device generates a three-dimensional model based on the bone library and then morphs (interpolates) that model to match the patient's specific geometry represented in the medical images.

In block 104, the model production device 10 parameterizes the model of the patient's bone to generate a parameterized model. A parameterized model includes a standardized or otherwise predetermined number of polygons or other facets (e.g., a standardized triangulation), and those polygons are arranged in a predetermined order relative to the patient's anatomy. For example, a polygon with a particular index or other position in the parameterized model may refer to a predetermined part of the patient's anatomy (e.g., polygon number 10,014 may refer to the peak of the lateral condyle in each parameterized model). In some embodiments, in block 106 the model production device 10 may standardize the number and position of triangles in the three-dimensional model relative to the patient's anatomy. The model production device 10 may use any appropriate technique to generate the parameterized model. For example, the model production device 10 may wrap the three-dimensional model to the parameterized model by performing principal component analysis, conformal point drift, or other parameterization techniques. Additionally or alternatively, in some embodiments the three-dimensional model of the patient's anatomy may be parameterized upon creation. For example, certain techniques for generating three-dimensional models based on two-dimensional medical images may automatically generate parameterized models. In those embodiments, the three-dimensional model of the patient's bone may be used as the parameterized model without additional processing by the model production device 10.

Figure 3:
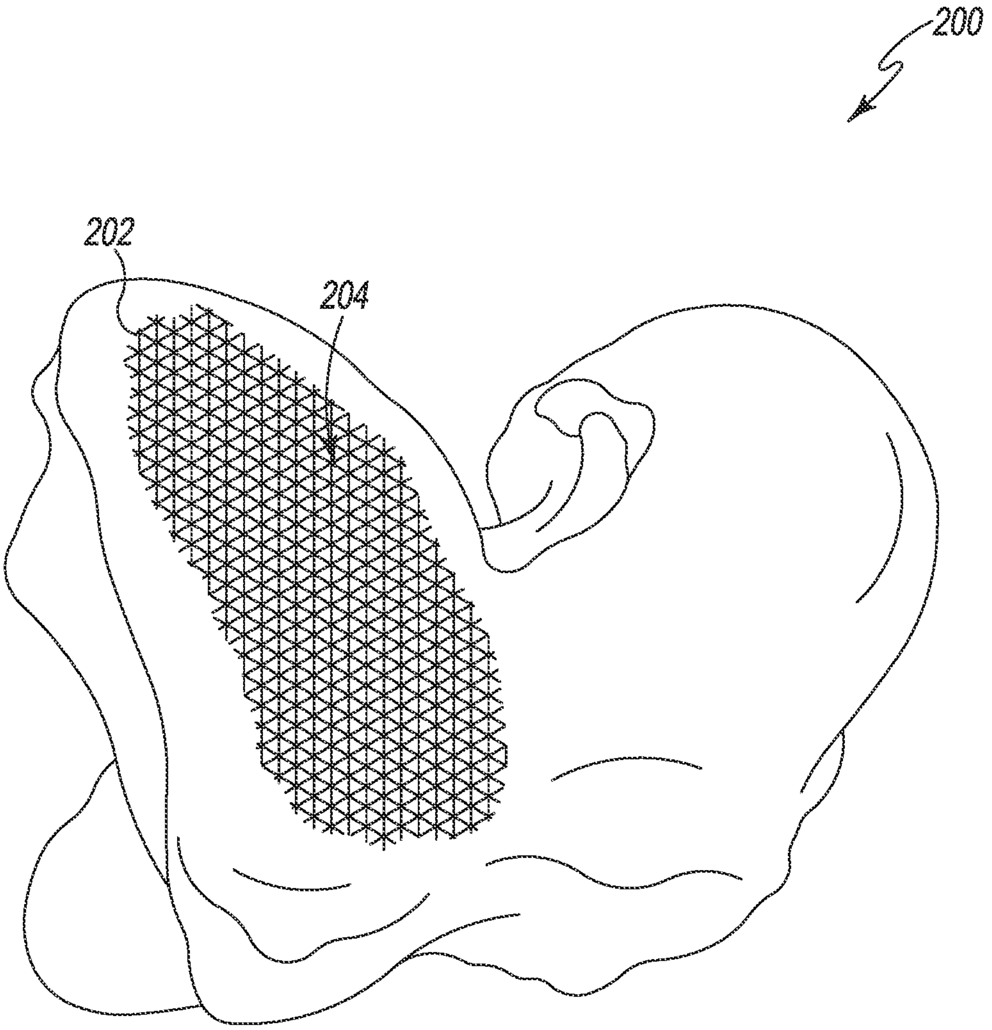
FIG. 3 is a schematic diagram of a parameterized model of a patient's femur that may be generated by the device of FIG. 1.

Referring now to FIG. 3, in an embodiment the model production device 10 may generate an illustrative parameterized model 200 as described above. The parameterized model 200 is based on three-dimensional model of a patient's femur, and may be used to generate a model for a femoral pin guide guide block, which is a customized patient-specific orthopaedic surgical instrument. Although illustrated in the present disclosure as a femoral pin guide block, it should be understood that the concepts of this disclosure may also be applied to other customized patient-specific orthopaedic surgical instruments, including femoral cutting blocks, tibial cutting blocks, drill/pin guides, milling guides, or other surgical guides.

As shown, the parameterized model 200 includes a predetermined number of triangles 202. Each of the triangles 200 is associated with a particular predetermined index or other position within the parameterized model 200 as well as a particular predetermined part of the patient's anatomy. For example, triangle 204 may be located at an index i within the parameterized model 200, and is positioned at a predetermined part of the condylar surface. Other parameterized models generated for other patient's femurs would also include a similar triangle 204 at the index i and positioned at the same predetermined part of the condylar surface. As described above, the parameterized model 200 may be generated based on a three-dimensional model of the patient's bone, or may be generated directly from two-dimensional medical images.

Referring back to FIGS. 2A and 2B, after generating or otherwise obtaining the parameterized model, in block 108, the model production device 10 determines a bounding spline of one or more contacting bodies of the to-be-manufactured patient-specific instrument based on the parameterized model. Each of the contacting bodies may be positioned in a predetermined location on the parameterized model. In some embodiments, each contacting body may be positioned in a location on the parameterized model having a higher accuracy. For example, parts of the model corresponding to silhouette curves of the bone visible in the medical images used to generate the three-dimensional model (e.g., epicondyle surfaces) may have higher accuracy as compared to other parts of the model (e.g., osteophytes).

In some embodiments, to determine a bounding spline, in block 110 the model production device 10 may identify a predetermined set of triangles in the parameterized model. Each identified triangle may have a predetermined index or other location in the parametric model and thus may correspond to a predetermined location on the patient's anatomy. For example, the model production device 10 may identify triangles on the condylar surfaces and the femoral cortex surface. The predetermined triangles may correspond to locations in the parametric model that are associated with accuracy or other confidence values that are above a predetermined threshold. For example, accuracy may be determined by comparing triangle positions in the parametric model with positions determined from a CT-scan-based model of the patient's bone. Average deviations may be determined for each triangle position based on such analysis of many parametric models of different bones. Triangles associated with a small deviation (e.g., less than 1 root-mean-square error (RMSE)) may be considered areas of high confidence, and triangles with a larger deviation (e.g., greater than or equal to 1 RMSE) may be considered areas of low confidence. The predetermined set of triangles may be identified as a set of triangles that surround areas of the parametric model that include triangles with high confidence. Of course, in other embodiments, different criteria may be used to identify areas of high confidence.

In block 112, the model production device 10 sets a key point for the bounding spline at the center of each identified, predetermined triangle. In block 114, the model production device 10 creates a bounding spline based on the key points. The bounding spline may be a Bezier spline or other curve defined based on the key points. In some embodiments, the model production device 10 may generate a polynomial equation to describe the curve defined by the key points. The polynomial may have a predetermined maximum degree. Thus, the bounding spline may be a smooth, relatively simple curve as compared to the parametric model and/or the three-dimensional model of the patient's anatomy.

Figure 4:
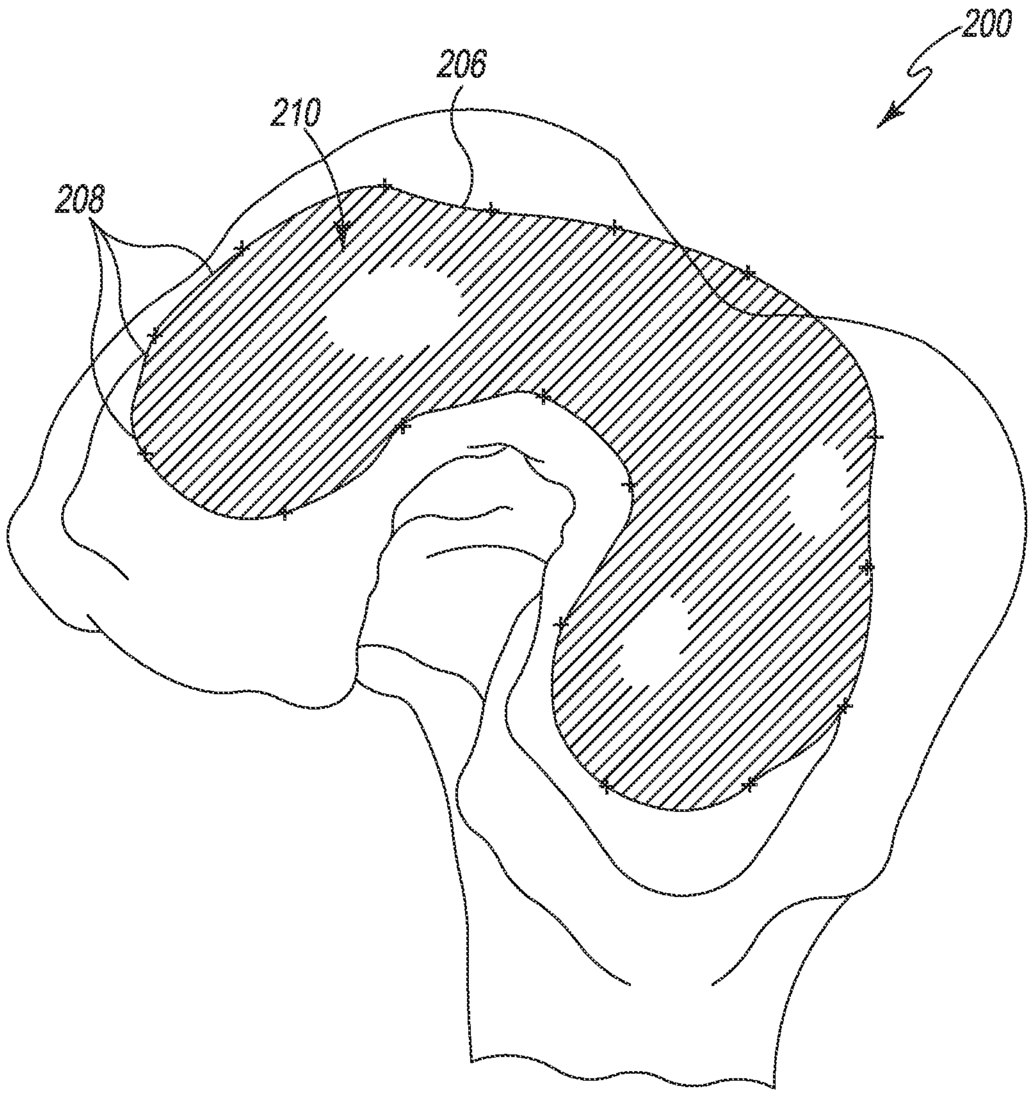
FIG. 4 is a schematic diagram of a bounding spline that may be generated by the device of FIG. 1 using the parametric model of FIG. 3.

Referring now to FIG. 4, an illustrative bounding spline 206 generated as described above is superimposed on the parameterized model 200. As shown, the illustrative bounding spline 206 surrounds part of the condylar surface of the parametric model 200. As described above, multiple key points 208 define the bounding spline 206. In particular, the key points 208 are control points for the bounding spline 206, which is illustratively a Bezier spline. As shown, the bounding spline 206 forms a smooth curve surrounding part of the parametric model 206.

Figure 5:
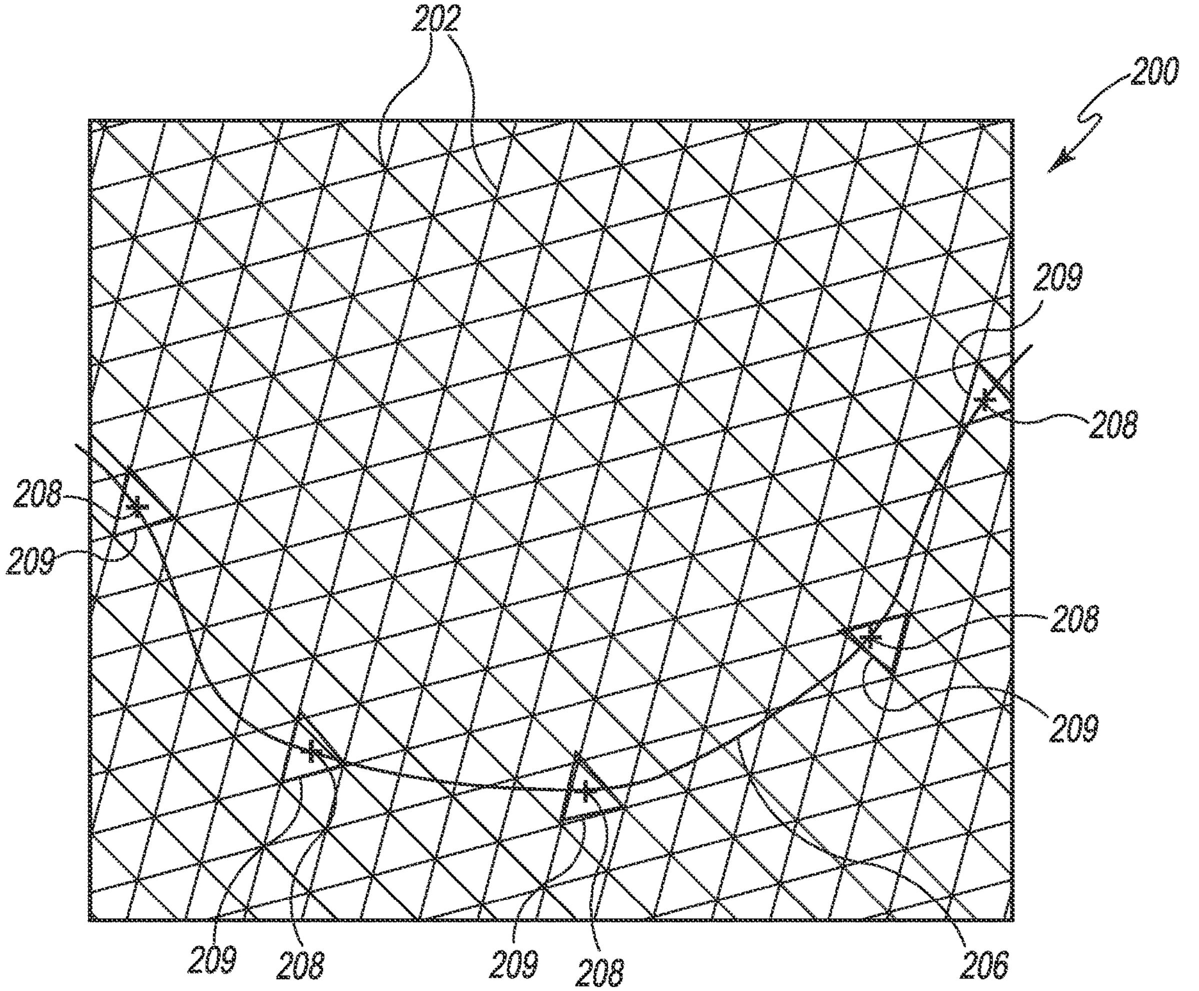
FIG. 5 is a schematic diagram of key points for the bounding spline of FIG. 4.

Referring now to FIG. 5, a detailed view of part of the bounding spline 206 is shown. The bounding spline 206 may be generated by identifying a set of predetermined triangles 209 as described above. As shown, each of the key points 208 may be determined by finding the center of a corresponding predetermined triangle 209. The bounding spline 206 smoothly connects those key points 208. As shown, the bounding spline 206 surrounds a number of triangles 202 of the parametric model 200. As described above, those triangles 202 may be associated with higher accuracy or otherwise be higher confidence as compared to triangles outside of the bounding spline 206.

Referring back to FIGS. 2A and 2B, after determining one or more bounding splines, in block 116, the model production device 10 creates a bounded surface based on each bounding spline. In the illustrative embodiment, the created bounded surface is embodied as a smooth surface surrounded by the bounding spline, such as a curved surface or a plane. As such, it should be appreciated that the bounded surface may not coincide with the surface of the parametric model; thus, the bounded surface may extend above and below the surface of the parametric model depending on, for example, the curvature of the bounding spline.

Referring again to FIG. 4, a bounded surface 210 has been created within the bounding spline 206 as described above. The illustrative bounded surface 210 is a smooth surface defined by the bounding spline 206, and not the parametric model 200. Thus, as shown, parts of the bounded surface 210 are positioned outside of the parametric model 200, and parts are positioned inside the parametric model 200. The illustrative bounded surface 210 is positioned on or near the condylar surface of the parameterized model 200. Additional bounded surfaces 210 may be generated in other positions of the parameterized model 200, such as the femoral cortex.

Referring back to FIGS. 2A and 2B, after generating one or more bounded surfaces, in block 118, the model production device 10 thickens each bounded surface to form the one or more contacting bodies. The contacting bodies may be included in a model for a patient-specific surgical instrument or other three-dimensional model. The model production device 10 thickens each bounded surface by extruding or otherwise extending the bounded surface both away from the parametric model (i.e., away from the center or surface of the model) and in towards the parametric model (i.e. toward the center or interior of the model). After thickening, each contacting body is intersected by the surface of the parametric model. In other words, after thickening, part of each contacting body is positioned both outside and inside of the parametric model.

Figure 6:
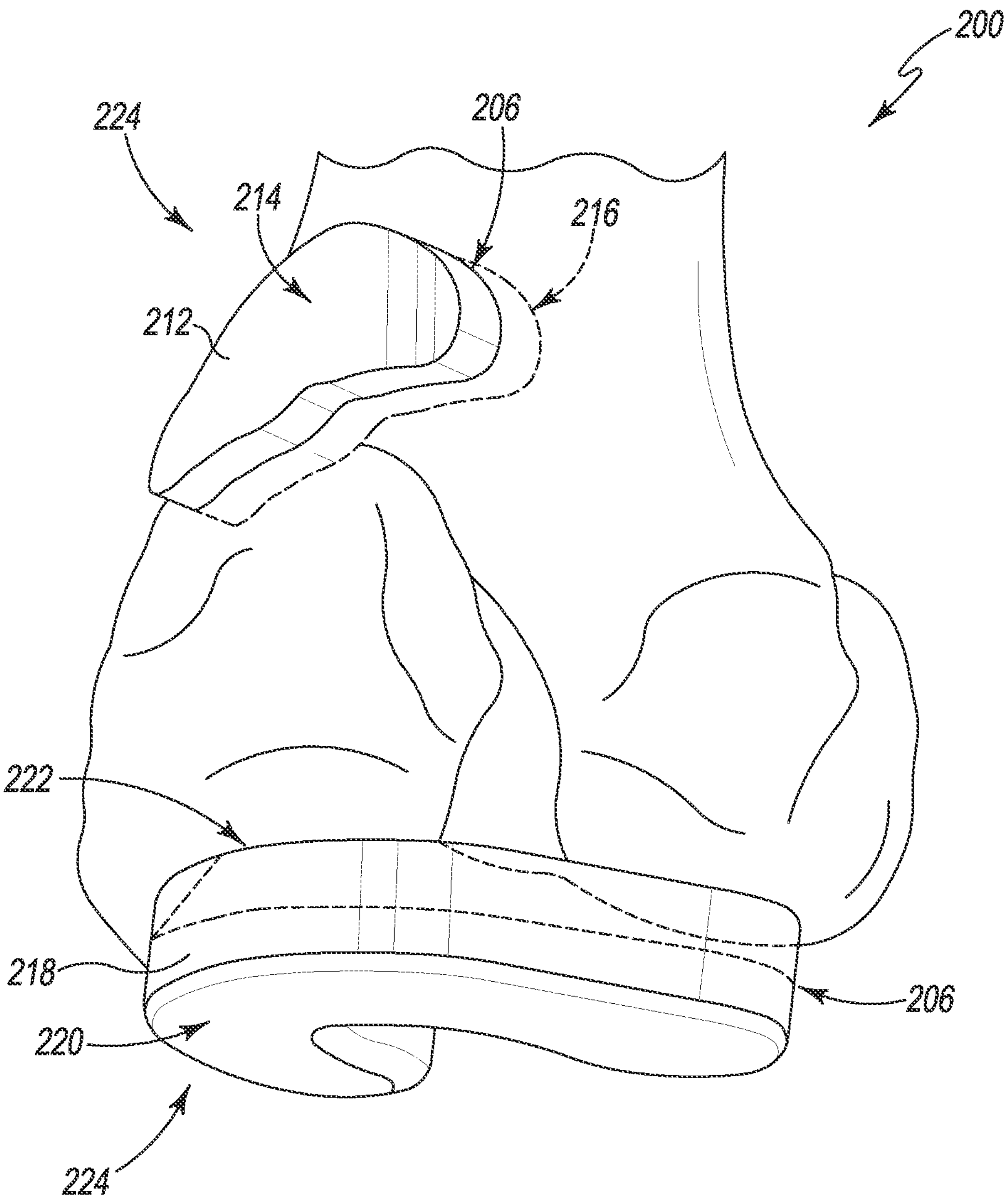
FIG. 6 is a schematic diagram of contacting bodies that may be generated by the device of FIG. 1 using the parametric model and bounding spline of FIGS. 3-5.

Referring now to FIG. 6, a pair of bounded surfaces 210 have been thickened into contacting bodies 212, 218 as described above. As shown, the contacting body 212 is positioned on the femoral cortex of the model 200 and the contacting body 218 is positioned on the condylar surface of the model 200. The contacting body 212 includes a surface 214 that is positioned away from the surface of the parametric model 200 and a surface 216 positioned within the surface of the parametric model 200. Similarly, the contacting body 218 includes a surface 220 that is positioned away from the surface of the parametric model 200 and a surface 222 positioned within the surface of the parametric model 200. Each of the contacting bodies 212, 218 has a perimeter defined by or is otherwise surrounded by a corresponding bounding spline 208. Similarly, each of those surfaces 214, 216 and surfaces 220, 222 may be defined by a corresponding bounded surface 210 that has been extended away from or within the parametric model 200. As shown, both of the contacting bodies 212, 218 intersect the surface of the parameterized model 200. That is, both contacting bodies 212, 218 extend both outside and inside the parameterized model 200. As shown, the contacting bodies 212, 218 are included in a model 224, which may be used to manufacture a patient-specific surgical instrument as described further below.

Referring back to FIG. 2, after creating the contacting bodies, in block 120, the model production device 10 adds one or more bridging bodies with parametric fixed geometry. The bridging bodies may connect one or more contacting bodies in the surgical instrument model. Each bridging body added to the surgical instrument model may be based on a fixed geometry that is parameterized based on the parameterized model. For example, the model production device 10 may adjust the length, width, thickness, or other dimension of a bridging body or other fixed geometry based on the size of an osteophyte or other feature in the parameterized model. The model production device 10 may determine the size of the feature based on the position or other dimensions of one or more predetermined polygons in the parametric model. As another example, the model production device 10 may adjust the starting point, ending point, or other position of the bridging body or other fixed geometry based on a feature in the parameterized model. Continuing that example, the model production device 10 may position the fixed geometry to connect to one or more of the contacting bodies that were generated as described above. Accordingly, the bridging bodies added to the surgical instrument model include patient-specific geometry that may be based on a unique combination of parameters such as width, length, thickness, and position.

Similar to the contacting bodies, the bridging bodies or other fixed geometry may intersect the surface of the parametrized model and thus extend both outside and inside the surface of the parameterized model. In some embodiments, in block 122 the parametric fixed geometry may be added at one or more high-contact areas of the parametric model to improve stability of the patient-specific surgical instrument. For example, the fixed geometry may be positioned to cross or otherwise engage a region of the patellofemoral osteophytes, which may provide significant stability in the flexion/extension degree of freedom. In some embodiments, the fixed geometry may be positioned in a lower-confidence part of the parameterized model. Positioning the fixed geometry in lower-confidence parts of the parameterized model may improve stability with less susceptibility to lower accuracy in the lower-confidence areas.

Figure 7:
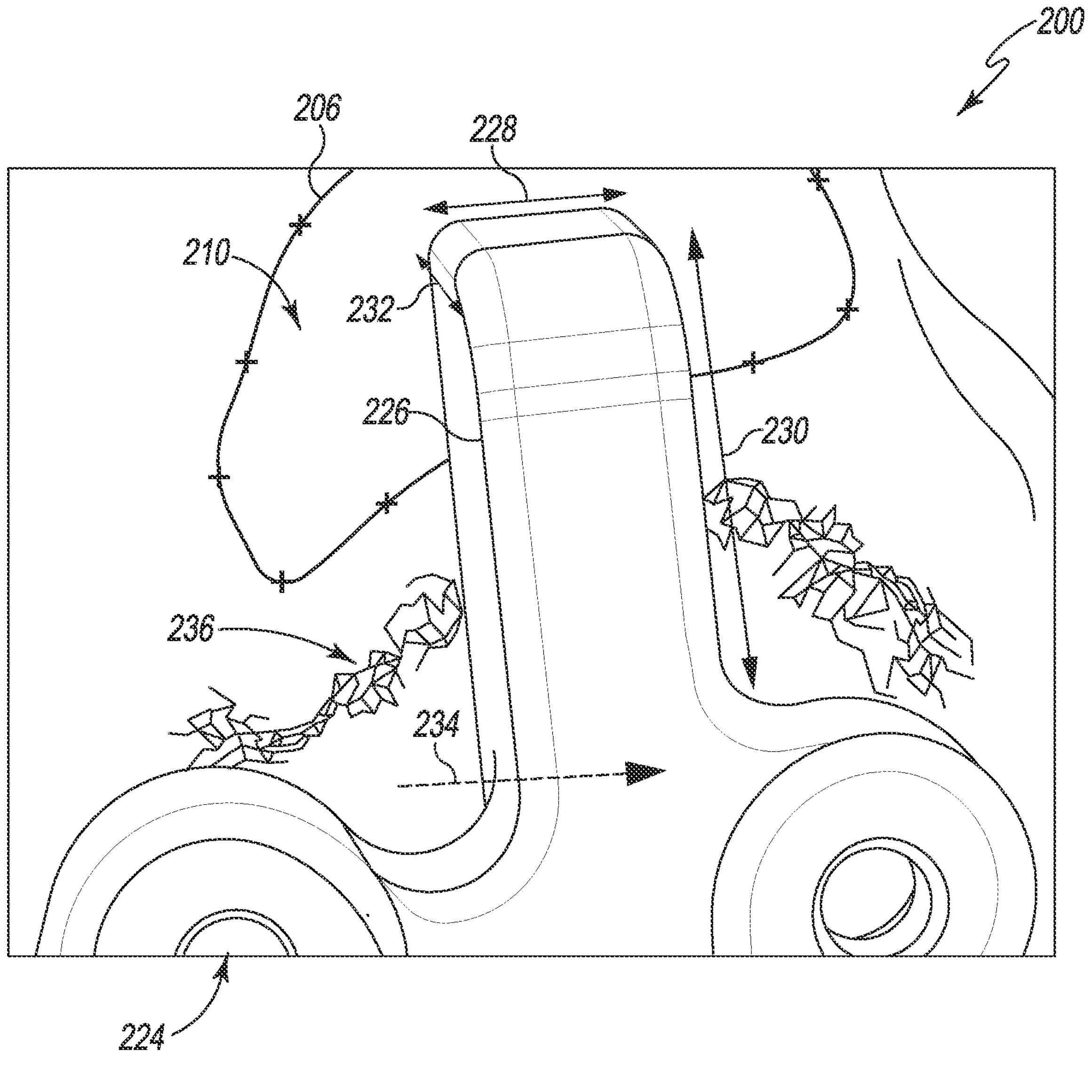
FIG. 7 is schematic diagram of a parametric fixed geometry that may be generated by the device of FIG. 1 using the parametric model of FIG. 3.

Referring now to FIG. 7, a bridging body 226 has been included in the model 224 of the patient-specific surgical instrument. As described above, the bridging body 226 is based on parameterized, fixed geometry. Thus, the bridging body 226 includes multiple parameters that may be adjusted based on the parametric model 200, including a width 228, a length 230, and a thickness 232. Additionally, a lateral position 234 of the bridging body 226 may also be adjusted.

As shown in FIG. 7, the lateral position 234 and/or the length 230 may be adjusted such that the bridging body 226 reaches the center of the bounded surface 210 on the femoral cortex. This will allow the bridging body to connect to a corresponding contacting body that is created as described above. Additionally, the illustrative bridging body 226 extends over a region of osteophytes 236 defined in the surface of the parameterized model 200. The width 228, length 230, and/or thickness 232 of the bridging body 226 may be adjusted based on the dimensions of the osteophytes 236. For example, the thickness 232 of the bridging body 226 may be adjusted to be larger than a height of the osteophytes 236 above the normal surface of the parameterized model 200 by a predetermined margin (e.g., four millimeters). The height of the osteophytes 236 may be determined by examining the position of a predetermined triangle in the parameterized model 200.

Referring back to FIGS. 2A and 2B, after adding the bridging bodies, in block 124, the model production device 10 may add parametric fixed geometry to the patient-specific surgical instrument model at one or more non-contacting locations. For example, the model production device 10 may add one or more cutting guides, bosses, drilling/fixation pin guides, milling guides, and/or other surgical guides to the patient-specific surgical instrument model. The added geometry connects to one or more of the contacting bodies and/or bridging bodies already included in the patient-specific surgical instrument model. However, the added features do not contact the surface of the parametric model.

Figure 8:
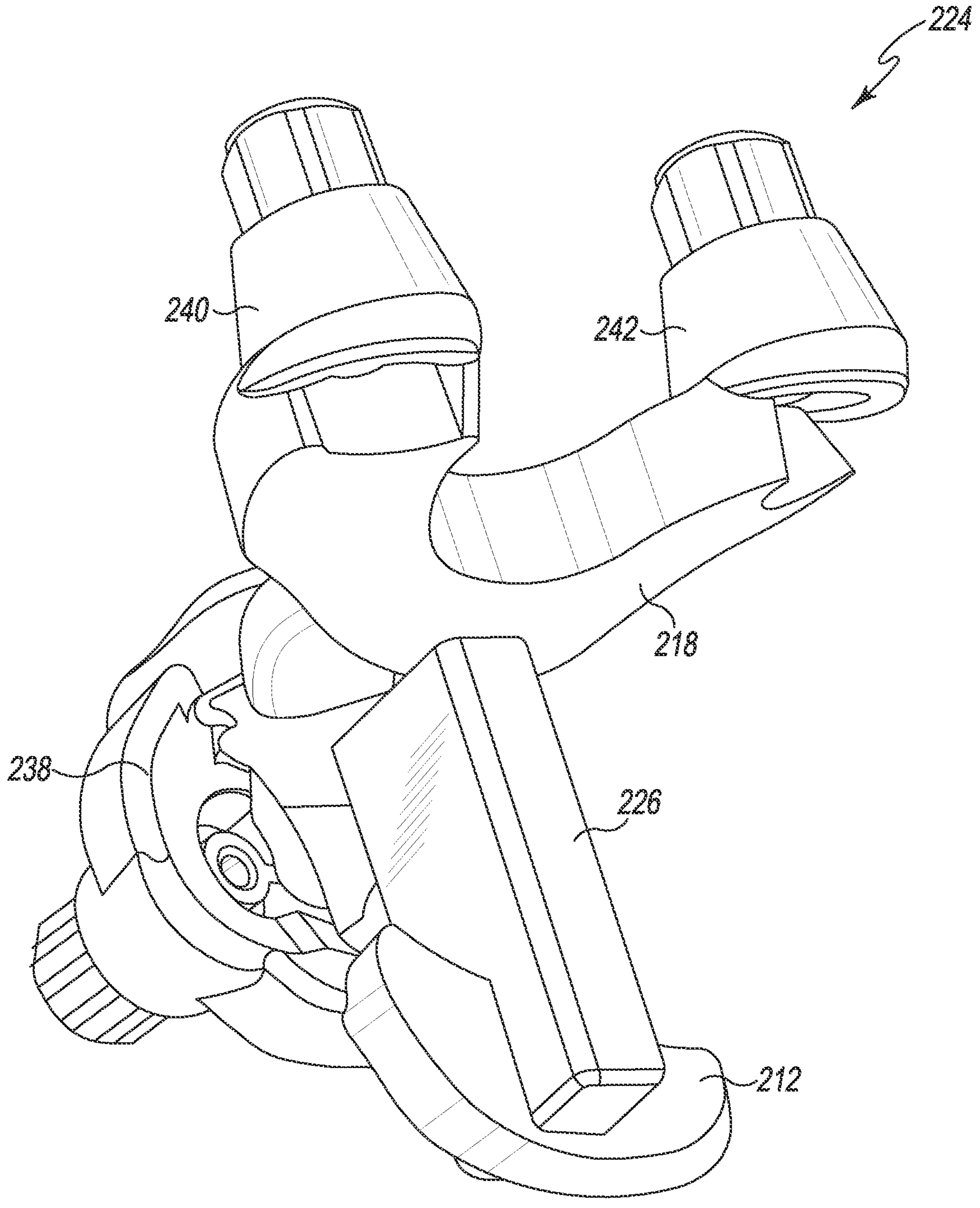
FIG. 8 is a schematic diagram of a patient-specific instrumentation model including the contacting bodies of FIG. 6 and the parametric fixed geometry of FIG. 7 that may be generated by the device of FIG. 1.

Referring now to FIG. 8, the illustrative model 224 of the patient-specific surgical instrument includes the contacting bodies 212, 218 added as described above in connection with block 118 and the parameterized bridging body 226 added as described above in connection with block 120. The model 224 also includes non-contacting fixed geometry that has been added as described above in connection with block 124. Illustratively, the non-contacting geometry includes a pin guide 238 and bosses 240, 242. As described above, the pin guide 238 and bosses 240, 242 may be based on predetermined, fixed geometry, such as a library of available pin guides, cutting guides, or other features. In some embodiments, attributes such as position and scale of the pin guide 238 and/or the bosses 240, 242 may be parameterized.

Referring back to FIGS. 2A and 2B, after adding fixed geometry to the patient-specific surgical instrument model, in block 126, the model production device 10 subtracts the patient bone model from the patient-specific instrumentation model to create one or more patient-specific contacting surfaces. Subtracting the patient bone model may remove geometry from the contacting bodies and/or the bridging bodies that extends within the patient bone model. Removing that geometry thus forms the patient-specific contacting surfaces on the contacting bodies and/or bridging bodies. Accordingly, the patient-specific contacting surface is a negative of the patient's bone model and thus is configured to engage the patient's bone. For example, the patient-specific contacting surface may include a unique set of depressions and ridges that are shaped to engage into a corresponding unique set of ridges and depressions of the patient's bone. The model production device 10 may subtract the parameterized model and/or the original three-dimensional model that was generated based on the surgical images, based on which model more accurately represents the patient's anatomy. For example, in embodiments in which the parameterization is not integrated into segmentation, the model production device 10 may subtract the original three-dimensional model. As another example, in embodiments in which the segmentation process directly produces a parameterized model, the model production device 10 may subtract the parameterized model. In some embodiments, the model production device 10 may enlarge the patient bone model by a small amount (e.g., a few millimeters) at certain locations to ensure that contact is prevented at non-contacting locations (e.g., to prevent contact between the patient's bone and non-contacting fixed geometry). In some embodiments, in block 128 the model production device 10 may subtract a parametrized cartilage model from the patient-specific instrumentation model.

Figure 9:
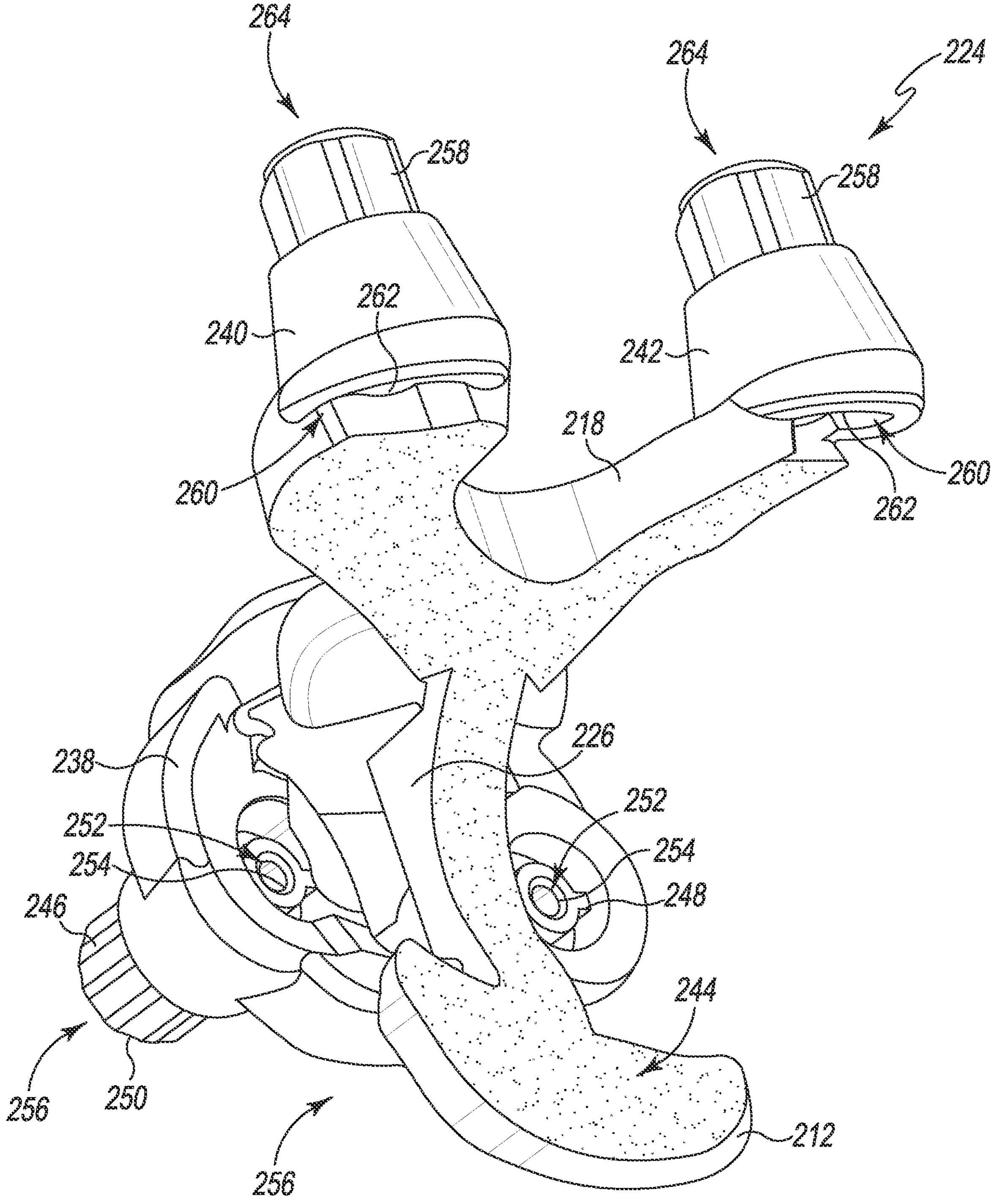
FIG. 9 is a schematic diagram of the patient-specific instrumentation model of FIG. 8 after subtraction of the patient's bony anatomy that may be generated by the device of FIG. 1.

Referring now to FIG. 9, the three-dimensional model of the patient's bone has been subtracted from the model 224 as described above. Subtracting the three-dimensional model creates a bone-contacting surface 244, which is a negative of the surface of the patient's bone and thus is configured to engage the patient's bone. For example, the bone-specific contacting surface 244 may include a unique set of depressions and ridges that are shaped to engage into a corresponding unique set of ridges and depressions of the patient's bone. As shown, the bone-contacting surface 244 forms a surface of the contacting bodies 212, 218 and the parametric, fixed geometry of the bridging body 226. The bone-contacting surface 244 is not a boundary of fixed non-contacting geometry such as the pin guide 238 and/or the bosses 240, 242. Additionally or alternatively, although illustrated as including a single bone-contacting surface 244, it should be understood that in some embodiments, the model 210 may include multiple bone-contacting surfaces 244. For example, in embodiments with multiple, disconnected contacting bodies, a bone-contacting surface 244 may be formed in each contacting body.

As shown in FIG. 9, the illustrative surgical instrument model 224 represents a femoral pin guide block. The surgical instrument model 224 thus includes a number of surgical tool guide bodies extending from the contacting bodies 212, 218 and/or the bridging body 226. Illustratively, the pin guide 238 includes a pair of bosses 246, 248 that extend outward from the pin guide 238 to a free end 250 that is spaced apart from the bridging body 226 and the contacting body 212. An opening 252 is defined in each of the bosses 246, 248. An inner wall 254 extends outwardly from the opening 252 to another opening defined in the free end 250. Thus, each boss 246, 248 defines a guide slot 256 extending through the pin guide 238. In the illustrative embodiment, each guide slot 256 is a drill guide and fixation pin guide hole, which is sized and shaped to guide a surgical drill to prepare the patient's bone to receive a fixation pin to couple the block to the bone.

Similarly, the bosses 240, 242 are coupled to the contacting body 218 and extend distally from the contacting body 218 to a free end 258. An opening 260 is defined in each of the bosses 240, 242, and an inner wall 262 extends outwardly from the opening 260 to another opening defined in the free end 258. Thus a guide slot 264 is defined through each boss 240, 242. Each guide slot 264 is a drill guide and fixation pin guide hole, which is sized and shaped to guide a surgical drill to prepare the patient's bone to receive a fixation pin to couple the block to the bone.

Referring back to FIGS. 2A and 2B, after subtracting the patient's bone model from the patient-specific surgical instrument model, in block 130, a customized patient-specific surgical instrument is manufactured based on the patient-specific surgical instrument model. In some embodiments, the model production device 10 may use the fabrication device 30 to manufacture the patient-specific surgical instrument, or the patient-specific surgical instrument may be manufactured by another device or process. The patient-specific surgical instrument may be fabricated using one or more forms of 3D printing or other additive manufacturing technology such as, for example, resin printing, optical fabrication, photo-solidification, or Direct Metal Laser Sintering (DMLS). Thus, the patient-specific surgical instrument may be illustratively formed from polymeric material. It should be understood that in some embodiments, the patient-specific surgical instrument may be formed from metallic material such as, for example, stainless steel. After manufacturing the patient-specific surgical instrument, the method 100 loops back to block 102, in which additional models may be generated and additional patient-specific surgical instruments may be manufactured.

Figure 10:
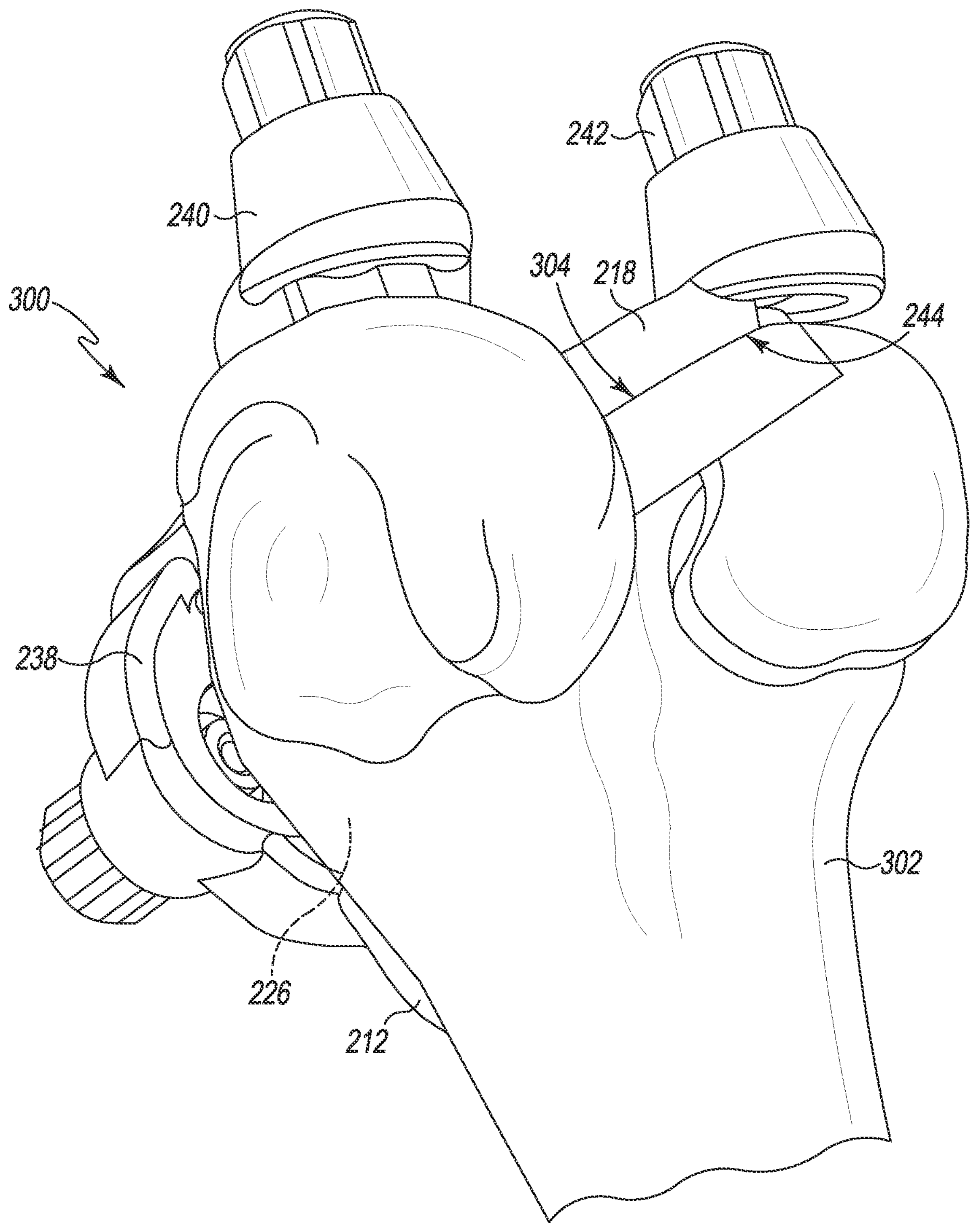
FIG. 10 is a perspective view of a customized patient-specific surgical instrument positioned on the patient's femur.

Referring now to FIG. 10, a patient-specific surgical instrument 300 has been manufactured based on the model 224 as described above. As described above, the customized patient-specific orthopaedic surgical instrument 300 is a femoral pin guide block in the illustrative embodiment. In the illustrative embodiment, the femoral pin guide block 300 is a single monolithic component formed from a polymeric material, such as polyphenylsulfone (PPSU), polyethylene, or another plastic material using an additive manufacturing process. In some embodiments, the femoral pin guide block 300 may be formed from a metallic material. As shown, the instrument 300 includes features represented in the model 224, included the contacting bodies 212, 218, the bridging body 226, the pin guide 238, the bosses 240, 242, and the bone-contacting surface 244. As shown, the surgical instrument 300 contacts the patient's femur 302 on a surface 304.

During use, a surgeon may prepare the patient's femur 302 by positioning the pin guide block 300 on the surface 304 of the femur 302. The bone-contacting surface 244 of the pin guide block 300 engages the surface 304 of the femur 302. After positioning the pin guide block 300 on the femur 302, the surgeon may then position a surgical drill or a self-drilling fixation pin in the guide slots 256 defined in the pin guide 238 and the guide slots 264 defined in each of the bosses 240, 242 to secure the pin guide block 300 to the patient's femur 302. A distal resection may then be performed on the distal end of the patient's femur 302 by advancing a surgical saw through a guide slot defined in the pin guide 238. In some embodiments, the fixation pins may be removed before the distal resection of the distal end of the patient's femur 302 so that the fixation pins do not interfere with the surgical saw.

It should be understood that in some embodiments, part or all of the operations of the method 100 shown in FIGS. 2A and 2B may be performed automatically by the model production device 10 or otherwise performed with limited user interaction. For example, in some embodiments, the model production device 10 may receive a three-dimensional model of a patient's bone and then automatically parameterize the bone using a wrapping process to generate a parameterized model. After generating the parameterized model, the model production device 10 may automatically determine bounding splines based on a predetermined list of triangles in the parametric model and then automatically generate contacting bodies from those bounding splines. Similarly, the model production device 10 may automatically adjust parameters of one or more bridging bodies based on one or more predetermined triangles in the parametric model. The model production device 10 may automatically add one or more predetermined fixed geometry to the model, and then automatically subtract the patient's bone model to generate the bone-contacting surfaces. Additionally or alternatively, in some embodiments, the model production device 10 may automatically generate part or all of the surgical instrument model and then allow a user to review and/or modify the generated surgical instrument model. Such embodiments may improve efficiency and reduce costs by reducing required user interaction as compared to previous techniques.

Figure 11:
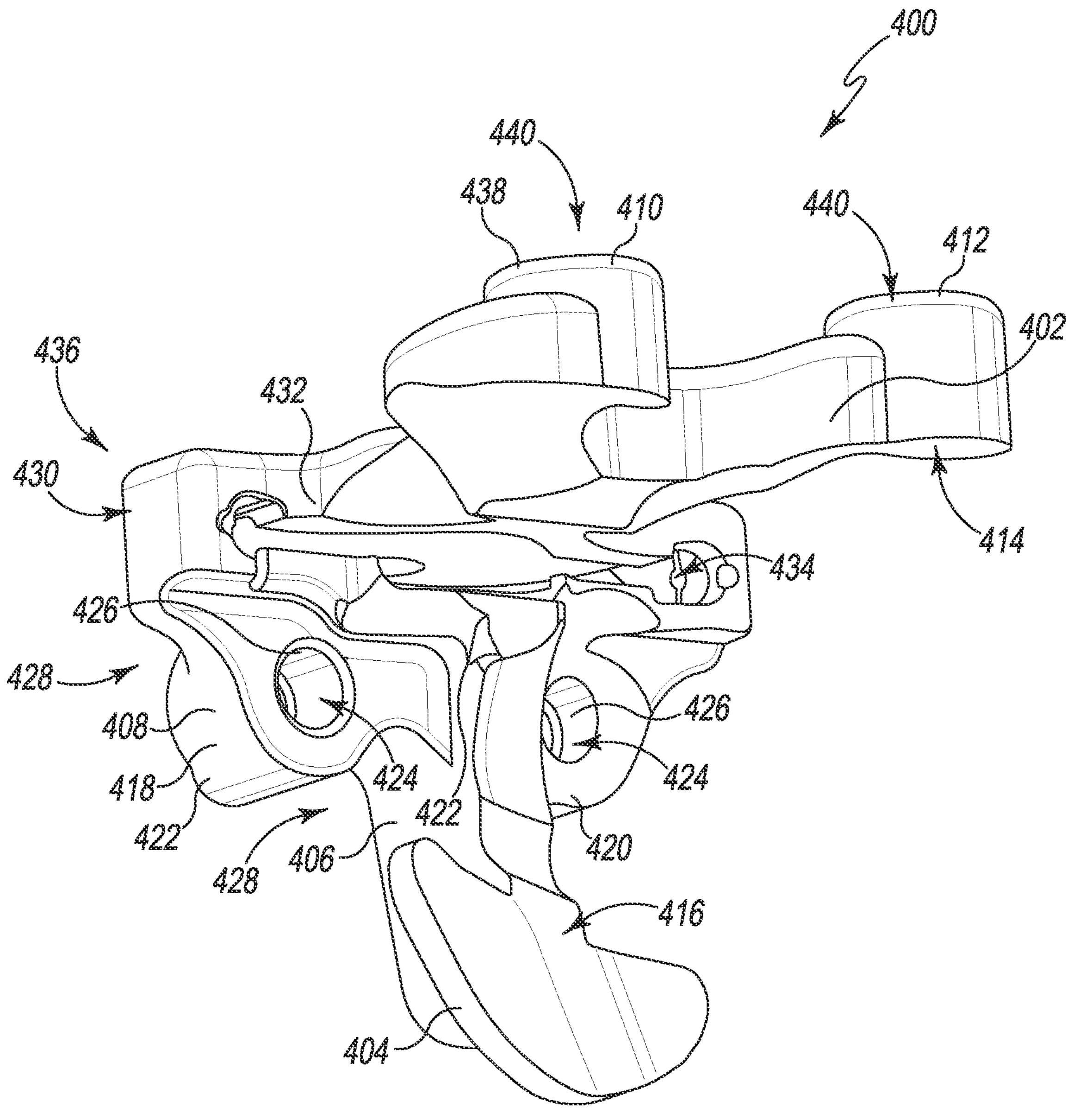
FIG. 11 is a schematic diagram of another patient-specific instrumentation model after subtraction of the patient's boney anatomy that may be generated by the device of FIG. 1.

Referring now to FIG. 11, in one embodiment, the model production device 10 may generate another surgical instrument model 400 for a femoral cutting guide block. Similar to the surgical instrument model 224, the surgical instrument model 400 includes contacting bodies 402, 404 generated from a parameterized model of the patient's bone as described above. The surgical instrument model 400 also includes a bridging body 406 coupled to the contacting body 404. The bridging body 406 is generated from parametric fixed geometry as described above. For example, the thickness, length, width, and position of the bridging body 406 may be determined based on the parametrized model of the patient's bone as described above. The surgical instrument model 400 also includes a cutting guide 408 and bosses 410, 412. The cutting guide 408 and bosses 410, 412 are generated from fixed geometry and may be parametrized as described above. As shown in FIG. 11, after subtraction of the patient's bone model, a bone-contacting surface 414 is formed on the contacting body 402, and another bone-contacting surface 416 is formed on the contacting body 404 and the bridging body 406. Each of the bone-contacting surfaces 414, 416 is a negative of a particular part of the patient's bone model and thus is configured to engage the patient's bone. As shown, the bone-contacting surfaces 414, 416 are separated by a guide slot of the cutting guide 408. Accordingly, the cutting guide 408 and the bosses 410, 412 do not include patient-contacting surfaces.

As shown in FIG. 11, the illustrative surgical instrument model 400 represents a femoral cutting guide block. The surgical instrument model 224 thus includes a number of surgical tool guide bodies extending from the contacting bodies 402, 404 and/or the bridging body 406. Illustratively, the cutting guide 408 includes a pair of bosses 418, 420 that extend outward to a free end 422 that is spaced apart from the bridging body 406 and the contacting body 404. An opening 424 is defined in each of the bosses 418, 420. An inner wall 426 extends outwardly from the opening 424 to another opening defined in the free end 422. Thus, each boss 418, 420 defines a guide slot 428 extending through the cutting guide 408. In the illustrative embodiment, each guide slot 428 is a drill guide and fixation pin guide hole, which is sized and shaped to guide a surgical drill to prepare the patient's bone to receive a fixation pin to couple the block to the bone.

The cutting guide 408 further includes an elongated opening 430 that is defined in the free end 422 and a number of inner walls 432 that extend inwardly from the opening 430. The inner walls 432 extend to another opening 434 that is defined in the cutting guide 408 between the bone-contacting surfaces 414, 416. The opening 434 cooperates with the inner walls 432 and the elongated opening 430 to define a guide slot 436, which is sized and shaped to guide a surgical tool such as, for example, a cutting blade, into engagement with the patient's bone.

As shown, the bosses 410, 412 are coupled to the contacting body 218 and extend distally from the contacting body 402 to a free end 438. An opening is defined in each of the bosses 410, 412, and an inner wall extends outwardly from the opening to another opening defined in the free end 438. Thus a guide slot 440 is defined through each boss 410, 412. Each guide slot 440 is a drill guide and fixation pin guide hole, which is sized and shaped to guide a surgical drill to prepare the patient's bone to receive a fixation pin to couple the block to the bone.

Figure 12:
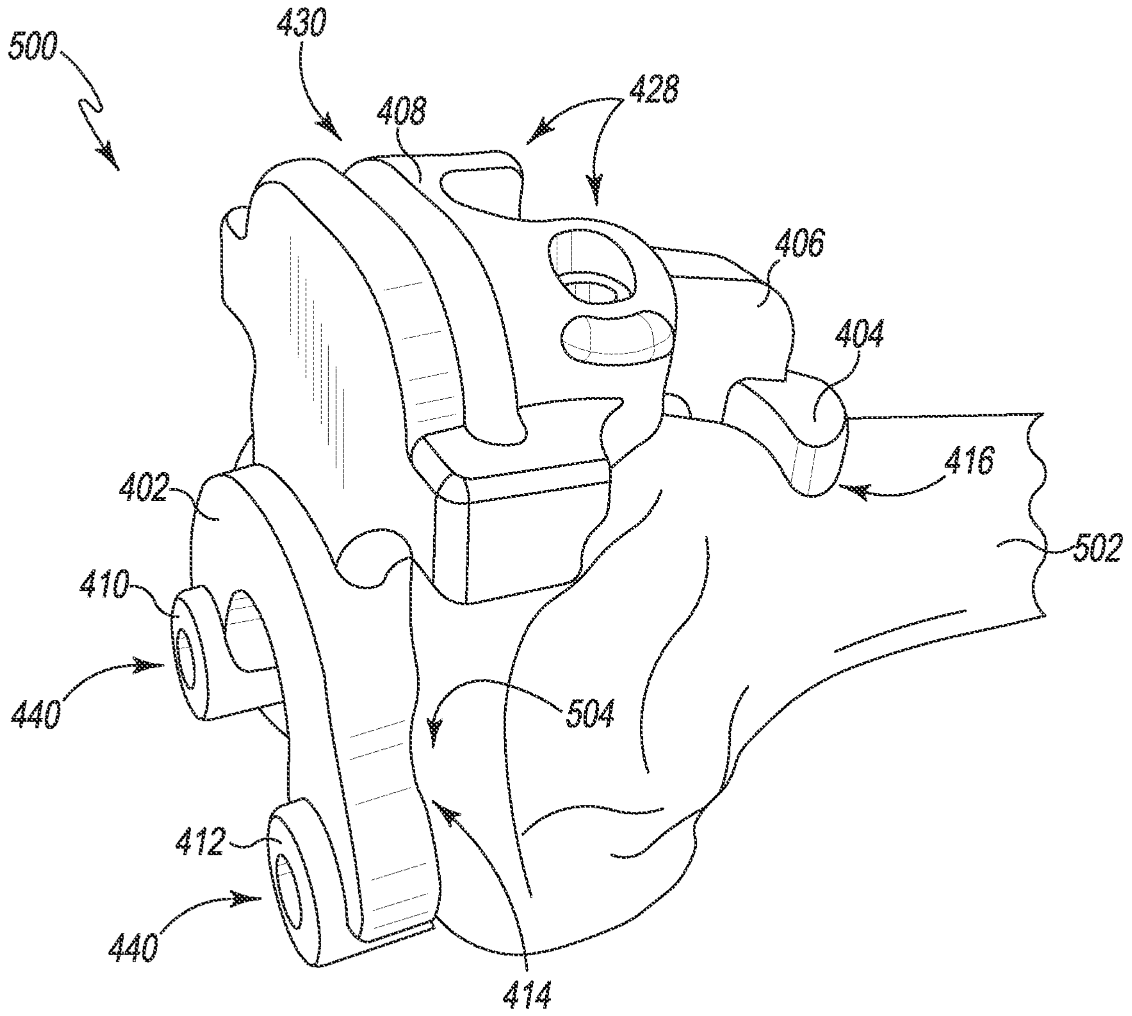
FIG. 12 is a perspective view of another customized patient-specific surgical instrument positioned on the patient's femur.

Referring now to FIG. 12, a patient-specific surgical instrument 500 has been manufactured based on the model 400 as described above. As described above, the customized patient-specific orthopaedic surgical instrument 500 is a femoral cutting guide block in the illustrative embodiment. In the illustrative embodiment, the femoral cutting block 500 is a single monolithic component formed from a polymeric material, such as polyphenylsulfone (PPSU), polyethylene, or another plastic material using an additive manufacturing process. In some embodiments, the femoral cutting block 500 may be formed from a metallic material. As shown, the instrument 500 includes features represented in the model 400, included the contacting bodies 402, 404, the bridging body 406, the cutting guide 408, the bosses 410, 412, and the bone-contacting surfaces 414, 416. As shown, the surgical instrument 500 contacts the patient's femur 502 on a surface 504.

During use, a surgeon may prepare the patient's femur 502 by positioning the cutting block 500 on the surface 504 of the femur 502. The bone-contacting surfaces 414, 416 of the cutting block 500 engage the surface 504 of the femur 502. After positioning the cutting block 500 on the femur 502, the surgeon may then position a surgical drill or a self-drilling fixation pin in the guide slots 428 defined in the cutting guide 408 and the guide slots 440 defined in each of the bosses 410, 412 to secure the cutting block 500 to the patient's femur 502. A distal resection may then be performed on the distal end of the patient's femur 502 by advancing a surgical saw through the guide slot 430 defined in the cutting guide 408. In some embodiments, the fixation pins may be removed before the distal resection of the distal end of the patient's femur 502 so that the fixation pins do not interfere with the surgical saw.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. One or more computer-readable media comprising a plurality of instructions that, when executed by a computing device, cause the computing device to:

generate a contacting body of a patient-specific surgical instrument model based on a parameterized model of a patient's bone, wherein the parameterized model comprises a predetermined number of polygons, and wherein each polygon has a predetermined position relative to the patient's anatomy, wherein to generate the contacting body comprises to: (i) determine a bounding spline based on a predetermined set of polygons of the parametrized model, (ii) generate a bounded surface surrounded by the bounding spline, and (iii) extend the bounded surface away from the parametrized model of the patient's bone and toward the parameterized model of the patient's bone to generate the contacting body, wherein the contacting body intersects a surface of the parameterized model;

add a bridging body connected to the contacting body of the patient-specific surgical instrument model based on the parameterized model, wherein the bridging body intersects the surface of the parametrized model and wherein the bridging body has a parametric fixed geometry, wherein to add the bridging body comprises to determine a parameter of the parametric fixed geometry of the bridging body based on the parameterized model; and subtract a three-dimensional model of the patient's bone from the patient-specific surgical instrument model to create a contacting surface, wherein the contacting surface is positioned on the contacting body and the bridging body.

2. The one or more computer-readable media of claim 1, further comprising a plurality of instructions that, when executed by the computing device, cause the computing device to manufacture a patient-specific surgical instrument based on the patient-specific surgical instrument model in response to subtraction of the three-dimensional model.

3. The one or more computer-readable media of claim 1, wherein the low-confidence part comprises a part of the parameterized model associated with a location of an osteophyte of the patient's bone, and wherein the high-confidence part comprises a part of the parameterized model associated with a location of a condylar surface or a femoral cortex of the patient's bone.

4. The one or more computer-readable media of claim 1, wherein the high-confidence part of the parameterized model includes polygons with an associated accuracy that exceeds a predetermined accuracy threshold.

5. The one or more computer-readable media of claim 1, wherein each polygon of the predetermined set of polygons has a predetermined index in the parameterized model.

6. The one or more computer-readable media of claim 1, wherein to determine the bounding spline comprises to:

identify the predetermined set of polygons;

set a control point at a center of each polygon of the predetermined set of polygons; and generate the bounding spline based on the control points.

7. The one or more computer-readable media of claim 1, wherein to determine the parameter of the parametric fixed geometry comprises to determine a length, a width, or a thickness based on a position of a polygon of the parametrized model.

8. The one or more computer-readable media of claim 1, wherein to determine the parameter of the parametric fixed geometry comprises to determine a location of the bridging body relative to the parameterized model.

9. The one or more computer-readable media of claim 8, wherein to determine the location of the bridging body relative to the parameterized model comprises to determine the location of the bridging body relative to the bounding spline.

10. The one or more computer-readable media of claim 1, further comprising a plurality of instructions that, when executed by the computing device, cause the computing device to add a second fixed geometry to the patient-specific surgical instrument model, wherein the second fixed geometry comprises a non-contacting surface.

11. The one or more computer-readable media of claim 1, further comprising a plurality of instructions that, when executed by the computing device, cause the computing device to:

generate the three-dimensional model of the patient's bone based on a plurality of images of the patient's bone; and parameterize the three-dimensional model of the patient's bone to generate the parameterized model.

12. The one or more computer-readable media of claim 1, further comprising a plurality of instructions that, when executed by the computing device, cause the computing device to generate the parameterized model based on a plurality of images of the patient's bone, wherein the parameterized model comprises the three-dimensional model.

13. The one or more computer-readable media of claim 1, wherein the patient-specific surgical instrument comprises a femoral cutting guide.

14. The one or more computer-readable media of claim 1, wherein to subtract the three-dimensional model comprises to subtract the three-dimensional model in response to adding the bridging body.

* * * * *